United States Patent
Lui et al.

(10) Patent No.: US 9,421,376 B2
(45) Date of Patent: Aug. 23, 2016

(54) SYSTEMS AND METHODS FOR ADJUSTING ELECTRICAL NEUROMODULATION THERAPY IN MEDICATION THERAPEUTIC WINDOW

(71) Applicant: BOSTON SCIENTIFIC NEUROMODULATION CORPORATION, Valencia, CA (US)

(72) Inventors: Mun Pook Lui, Northridge, CA (US); Sridhar Kothandaraman, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 95 days.

(21) Appl. No.: 14/107,979

(22) Filed: Dec. 16, 2013

(65) Prior Publication Data

US 2014/0180349 A1    Jun. 26, 2014

Related U.S. Application Data

(60) Provisional application No. 61/745,220, filed on Dec. 21, 2012.

(51) Int. Cl.
| | |
|---|---|
| *A61N 1/00* | (2006.01) |
| *A61N 1/36* | (2006.01) |
| *A61M 5/172* | (2006.01) |
| *A61N 1/372* | (2006.01) |

(52) U.S. Cl.
CPC ........ *A61N 1/36139* (2013.01); *A61M 5/1723* (2013.01); *A61N 1/37235* (2013.01)

(58) Field of Classification Search
CPC ....... A61N 1/0412–1/048; A61N 1/30–1/306; A61N 1/325; A61N 1/327; A61N 1/36128; A61N 1/36139; A61N 1/37235; A61N 1/3605; A61N 1/37247; A61M 5/1723; A61M 2037/0007
See application file for complete search history.

(56) References Cited

U.S. PATENT DOCUMENTS

| | | | |
|---|---|---|---|
| 6,128,537 A * | 10/2000 | Rise | 607/45 |
| 6,393,325 B1 | 5/2002 | Mann et al. | |
| 6,516,227 B1 | 2/2003 | Meadows et al. | |
| 6,845,267 B2 * | 1/2005 | Harrison et al. | 607/3 |

(Continued)

OTHER PUBLICATIONS

U.S. Appl. No. 61/080,187, System and Method for Converting Tissue Stimulation Programs in a Format Usable by an Electrical Current Steering Navigator, Inventor: James R. Thacker, filing date: Jul. 11, 2008.

(Continued)

*Primary Examiner* — Mallika D Fairchild
(74) *Attorney, Agent, or Firm* — Schwegman Lundberg & Woessner, P.A.

(57) ABSTRACT

A neuromodulation system and method for managing electrical neuromodulation therapy for a patient in conjunction with administering a pharmacological agent to the patient. Electrical energy is delivered to a target tissue region of the patient, thereby electrically modulating the target tissue region providing therapy to the patient. The energy level of the electrical energy delivered to the tissue is automatically varied inversely to the effect of the pharmacological agent on the patient during a therapeutic window. An absorption level of the pharmacological agent in the patient may be continually detected, and the energy level of the delivered electrical energy automatically varied based on the detected absorption level of the pharmacological agent during a therapeutic window.

20 Claims, 8 Drawing Sheets

(56) References Cited

U.S. PATENT DOCUMENTS

| | | |
|---|---|---|
| 6,895,280 B2 | 5/2005 | Meadows et al. |
| 6,993,384 B2 | 1/2006 | Bradley et al. |
| 7,539,538 B2 | 5/2009 | Parramon et al. |
| 7,650,184 B2 | 1/2010 | Walter |
| 8,019,439 B2 | 9/2011 | Kuzma et al. |
| 2003/0139781 A1 | 7/2003 | Bradley et al. |
| 2005/0267546 A1 | 12/2005 | Parramon et al. |
| 2007/0168004 A1 | 7/2007 | Walter |
| 2007/0168007 A1 | 7/2007 | Kuzma et al. |

OTHER PUBLICATIONS

U.S. Appl. No. 61/646,773, System and Method for Shaped Phased Current Delivery, Inventor: Kerry Bradley, filing date: May 14, 2012.

* cited by examiner

SYSTEMS AND METHODS FOR ADJUSTING ELECTRICAL NEUROMODULATION THERAPY IN MEDICATION THERAPEUTIC WINDOW

RELATED APPLICATION DATA

The present application claims the benefit under 35 U.S.C. §119 to U.S. provisional patent application Ser. No. 61/745,220, filed Dec. 21, 2012. The foregoing application is hereby incorporated by reference into the present application in its entirety.

FIELD OF THE INVENTION

The present invention relates to tissue stimulation systems generally, and particularly, to therapy management systems and methods.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have been accepted as a therapeutic modality for the treatment of chronic neuropathic pain syndromes. The application of spinal cord stimulation has expanded to include additional applications, such as angina pectoralis, peripheral vascular disease, and incontinence, among others. Spinal cord stimulation is also a promising option for patients suffering from neuro-motor disorders, such as Parkinson's Disease, Dystonia and essential tremor.

An implantable SCS system typically includes electrode-carrying stimulation leads and neurostimulator. The stimulation leads are implanted at a stimulation site in proximity to the spinal cord tissue of the patient. The neurostimulator implanted remotely from the stimulation site, but coupled either directly to the stimulation lead(s) or indirectly to the stimulation lead(s) via a lead extension. The neurostimulation system may further include a handheld patient programmer to instruct the neurostimulator remotely for generating electrical stimulation pulses in accordance with selected stimulation parameters. The handheld patient programmer may, itself, be programmed by a technician attending the patient, for example, by using a Clinician's Programmer (CP), which typically includes a general purpose computer, such as a laptop, desktop, tablet computer or any other suitable computer having a programming software package installed thereon.

Thus, applied programmed electrical pulses can be delivered from the neurostimulator to the stimulation lead(s) to stimulate or activate a volume of the spinal cord tissue. Specifically, electrical stimulation energy conveyed to the electrodes creates an electrical field, which when strong enough, depolarizes (or "stimulates") the neural fibers within the spinal cord beyond a threshold level. As a result, the firing of action potentials (APs) is induced that propagate along the neural fibers to provide the desired efficacious therapy to the patient.

Traditionally, a combination of such neurostimulation therapy and pharmacological therapy is prescribed for delivering fast relief to or against certain chronic diseases or disorders in a patient. The effectiveness of the pharmacological therapy changes during its therapeutic window. As a result, to maintain a positive net effect of neurostimulation therapy and pharmacological therapy, the patient manually adjusts the applied level of electrical stimulation energy during the therapeutic window. Such adjustment may temporally differ relative to the changing effectiveness of the pharmacological therapy within its therapeutic window. Consequently, the action of neurostimulation therapy may become unsynchronized with that of the pharmacological therapy and may disturb the overall treatment regime.

Therefore, there exists a need for a solution for synchronizing electrical stimulation therapy with the changing effect of pharmacological therapy.

SUMMARY OF THE INVENTION

In accordance with a first aspect of the present inventions, a neuromodulation system for managing electrical neuromodulation therapy for a patient in conjunction with administering a pharmacological agent to the patient is provided. The neuromodulation system comprises output modulation circuitry configured for delivering electrical energy to a target tissue region of the patient, thereby electrically modulating the target tissue region providing therapy to the patient. The neuromodulation system further comprises a controller/processor configured for automatically instructing the output modulation circuitry to vary the energy level of the electrical energy delivered to the tissue inversely to the effect of the pharmacological agent on the patient during a therapeutic window. Such automatic instruction of the modulation output circuitry can be triggered, e.g., in response to the user input. If the electrical energy comprises pulsed electrical energy, the controller/processor may be configured for automatically instructing the output modulation circuitry to automatically vary the level of the electrical energy by adjusting one or both of a pulse amplitude and a pulse width of the pulsed electrical energy.

The pharmacological agent may have a relatively strong effect during a first time period of the therapeutic window and a relatively weak effect during a second time period subsequent to the first time period, in which case, the controller/processor may be configured for automatically instructing the output modulation circuitry to deliver the electrical energy to the tissue at a relatively low level during the first time period and at a relatively high level during the second time period. In one embodiment, the neuromodulation system further comprises memory configured for storing a pre-defined reference curve, in which case, the controller/processor may be configured for automatically instructing the output modulation circuitry to vary the energy level of the electrical energy delivered to the tissue in accordance with the pre-defined reference curve. In another embodiment, the neuromodulation system further comprises monitoring circuitry configured for detecting an absorption level of the pharmacological agent in the patient, in which case, the controller/processor may be configured for automatically instructing the output modulation circuitry to vary the energy level of the electrical energy delivered to the tissue based on the detected absorption level of the pharmacological agent.

In accordance with a second aspect of the present inventions, a method for managing electrical neuromodulation therapy for a patient in conjunction with administering a pharmacological agent to the patient is provided. The method comprises delivering electrical energy to a target tissue region of the patient, thereby electrically modulating the target tissue region providing therapy to the patient, and automatically varying the energy level of the electrical energy delivered to the tissue inversely to the effect of the pharmacological agent on the patient during a therapeutic window. Such automatic varying of the modulation output circuitry can be triggered, e.g., in response to the user input. If the electrical energy comprises pulsed electrical energy, the energy level of may be automatically varied by adjusting one or both of a pulse amplitude and a pulse width of the pulsed electrical energy.

The pharmacological agent may have a relatively strong effect during a first time period of the therapeutic window and a relatively weak effect during a second time period subsequent to the first time period, in which case, the energy level of the electrical energy delivered to the tissue may be relatively low during the first time period and relatively high during the second time period. In one method, the energy level of the electrical energy delivered to the tissue is automatically varied in accordance with a pre-defined electrical modulation curve. Another method further comprises continually detecting an absorption level of the pharmacological agent in the patient, in which case, the energy level of the electrical energy delivered to the tissue may be automatically varied based on the detected absorption level of the pharmacological agent.

In accordance with a third aspect of the present inventions, another neuromodulation system for managing electrical neuromodulation therapy for a patient in conjunction with administering a pharmacological agent to the patient is provided. The neuromodulation system comprises output modulation circuitry configured for delivering electrical energy to a target tissue region of the patient, thereby electrically modulating the target tissue region and providing therapy to the patient, and monitoring circuitry configured for continually monitoring an absorption level of the pharmacological agent in the patient.

The neuromodulation system further comprises a controller/processor configured for automatically instructing the output modulation circuitry to vary the energy level of the electrical energy delivered to the tissue during a therapeutic window based on the detected absorption level of the pharmacological agent. Such automatic instruction of the modulation output circuitry can be triggered, e.g., in response to the user input. If the electrical energy comprises pulsed electrical energy, the controller/processor may be configured for automatically instructing the output modulation circuitry to automatically vary the level of the electrical energy by adjusting one or both of a pulse amplitude and a pulse width of the pulsed electrical energy. The monitored pharmacological agent may have a relatively strong effect during a first time period of the therapeutic window and a relatively weak effect during a second time period subsequent to the first time period, in which case, the controller/processor may be configured for automatically instructing the output modulation circuitry to deliver the electrical energy to the tissue at a relatively low level during the first time period and at a relatively high level during the second time period.

In accordance with a fourth aspect of the present inventions, another method for managing electrical neuromodulation therapy for a patient in conjunction with administering a pharmacological agent to the patient is provided. The method comprises delivering electrical energy to a target tissue region of the patient, thereby electrically modulating the target tissue region providing therapy to the patient, and continually detecting an absorption level of the pharmacological agent in the patient. The method further comprises automatically varying the energy level of the electrical energy delivered to the tissue based on the detected absorption level of the pharmacological agent during a therapeutic window. Such automatic varying of the modulation output circuitry can be triggered, e.g., in response to the user input.

If the electrical energy comprises pulsed electrical energy, the energy level of may be automatically varied by adjusting one or both of a pulse amplitude and a pulse width of the pulsed electrical energy. Continually detecting the absorption level of the pharmacological agent in the patient may comprise detecting a relatively high absorption level of the pharmacological agent during a first time period of the therapeutic window and detecting a relatively low absorption level during a second time period subsequent to the first time period, in which case, the energy level of the electrical energy delivered to the tissue may be relatively low during the first time period and relatively high during the second time period.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained; a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
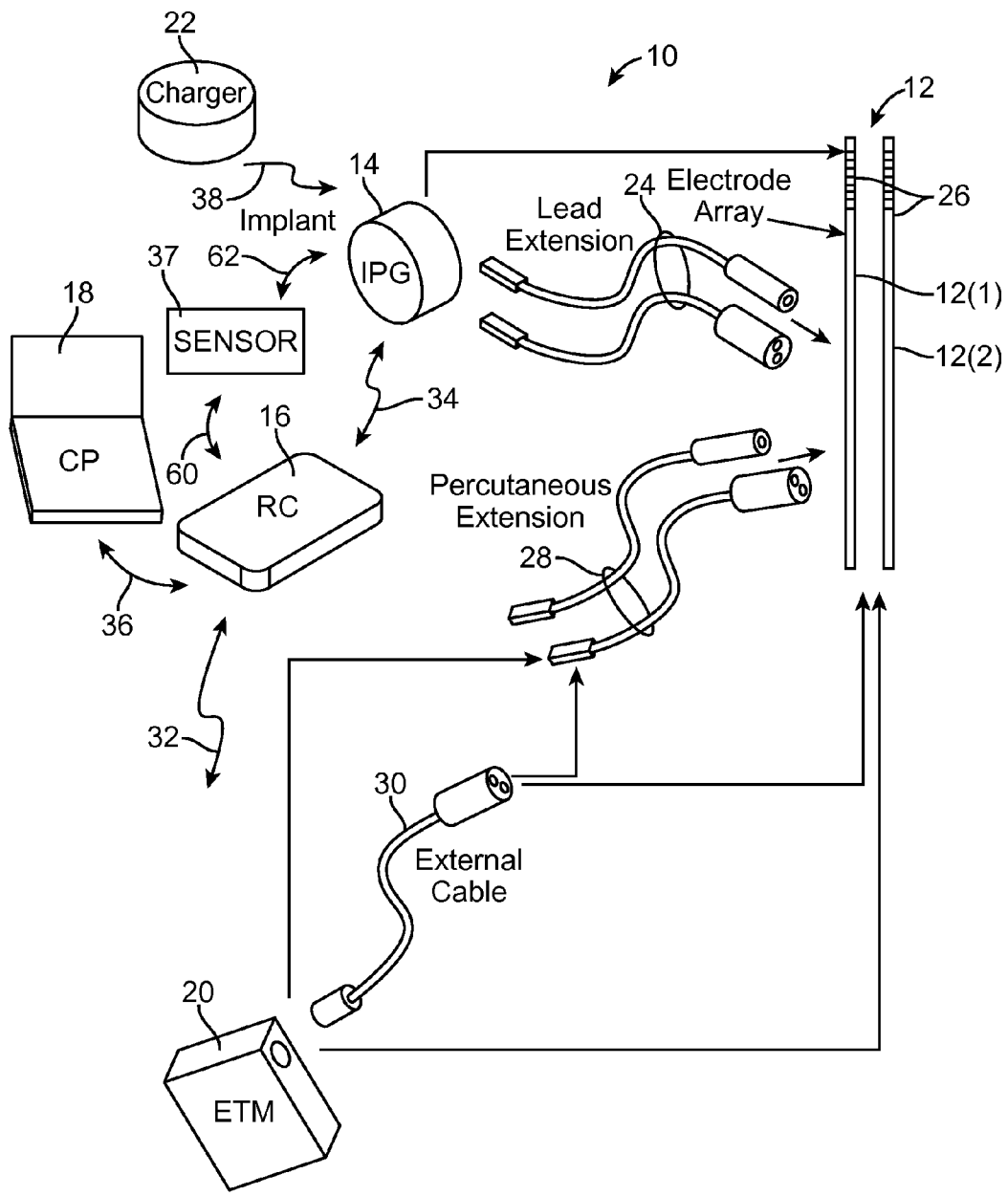
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), an implantable pulse generator (IPG) 14, an external remote controller RC 16, a clinician's programmer (CP) 18, an External Trial Modulator (ETM) 20, an external charger 22, and a sensor 37. The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 are arranged in-line along the modulation leads 12. As will be described in further detail below, in alternative embodiments, the electrodes 26 may be arranged in a two-dimensional pattern on a single paddle lead or arranged in a circular pattern on a cuff lead. As will be described in further detail below, the IPG 14 includes pulse generation circuitry that delivers electrical modulation energy (e.g., electrical stimulation energy) in the form of an electrical pulse train to the electrode array 26 in accordance with a set of modulation parameters.

The ETM 20 may also be physically connected via the percutaneous lead extensions 28 and external cable 30 to the modulation leads 12. The ETM 20, which has similar pulse generation circuitry as the IPG 14, also delivers electrical modulation energy in the form of an electrical pulse train to the electrode array 26. The major difference between the ETM 20 and the IPG 14 is that the ETM 20 is a non-implantable device that is used on a trial basis after the modulation leads 12 have been implanted and prior to implantation of the IPG 14, to test the responsiveness of the modulation that is to be provided. Thus, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions. The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Further, the SCM system 10 includes a sensor 37 configured to detect the presence of pharmacological agent within the body and communicate the information related to such detection to the IPG 14. For this, a number of conventional sensing devices and techniques are available to the art. The sensor 37 may be implanted within the patient's body, or one could employ a sensor 37 capable of remotely sensing the desired parameter from a position outside the patient's body. Alternatively, the sensor 37 may be integrally manufactured with the casing of IPG 14. In either instance, the sensor 37 communicates with the IPG 14 and the external RC 16 via bi-directional communication links 62 and 60, respectively, or via an electrical conductor (not shown). The communication links 62 and 60 may function via RF or other suitable technology.

Figure 2:
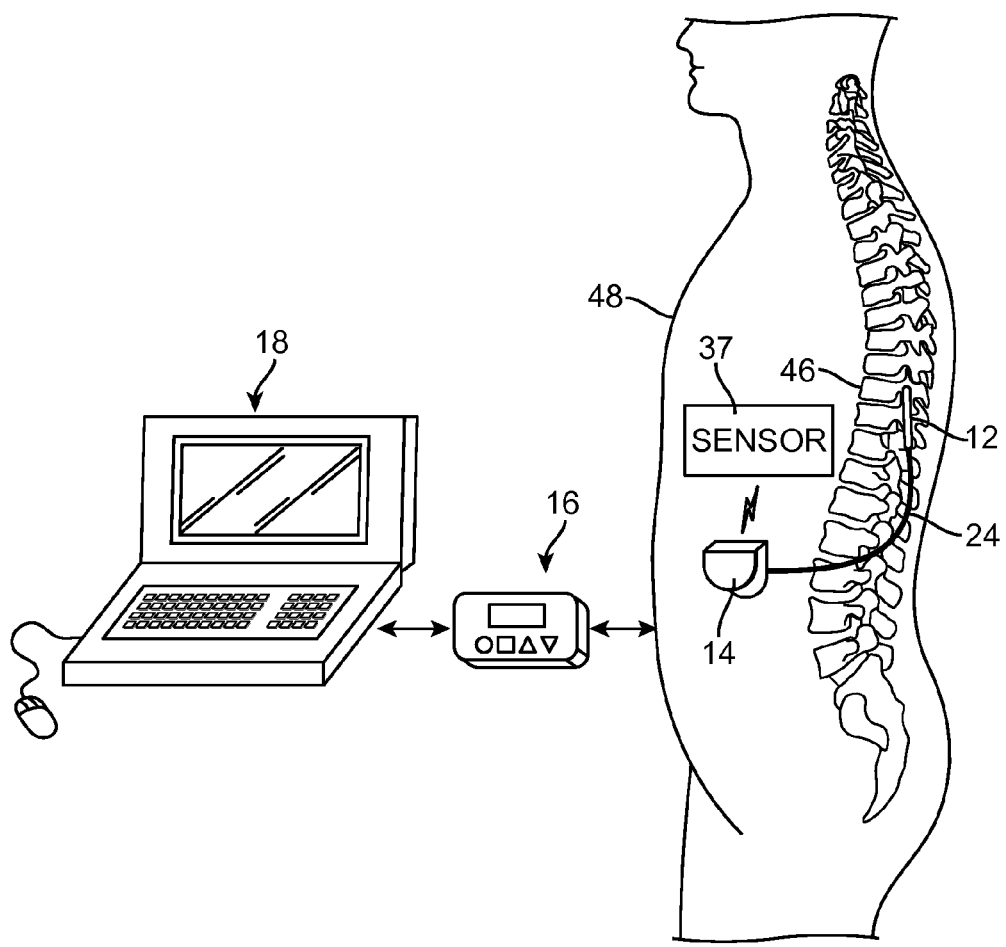
FIG. 2 is a plan view of the SCM system of FIG. 1 in use with a patient.

As shown in FIG. 2, the modulation leads (or lead) 12 are implanted within the spinal column 46 of a patient 48. The preferred placement of the modulation leads 12 is adjacent, i.e., resting near, or upon the dura, adjacent to the spinal cord area to be stimulated. The modulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

The overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, the programming methodologies can be performed using firmware or hardware. In any event, the CP 18, under the control of the clinician, may actively control the characteristics of the electrical modulation energy generated by the IPG 14 to allow the optimum stimulation parameters to be determined based on patient feedback and for subsequently programming the IPG 14 with the optimum stimulation parameters.

Figure 3:
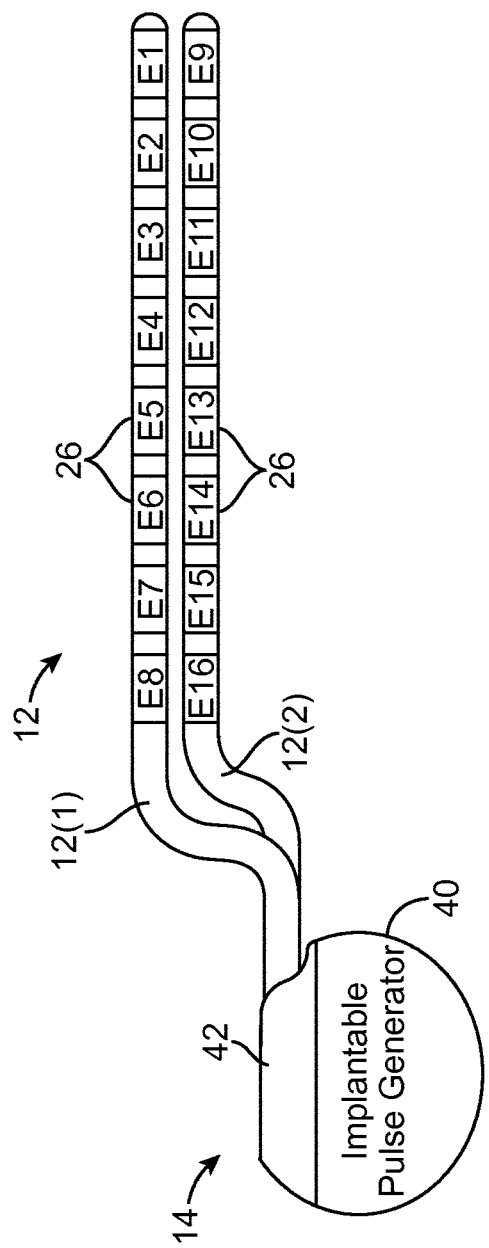
FIG. 3 is a profile view of an implantable pulse generator (IPG) and percutaneous leads used in the SCS system of FIG. 1.

Referring to FIG. 3, the IPG 14 comprises an outer case 40 for housing the electronic and other components (described in further detail below), and a connector 42 to which the proximal end of the neuromodulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

In the embodiment illustrated in FIG. 3, the neuromodulation leads 12 take the form of percutaneous leads on which the electrodes 26 (in this case, electrodes E1-E16) are disposed as ring electrodes. In the illustrated embodiment, two percutaneous leads 12(1) and 12(2) on which electrodes E1-E8 and E9-E16 are respectively disposed can be used with the SCM system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The SCM system 10 utilizes a technique that dynamically manages electrical modulation therapy for a patient in conjunction with administering a pharmacological agent to the patient. The RC 16 and/or the CP 18 telemetrically communicates and configures the IPG 14 to automatically vary the energy level of the electrical energy delivered to a target tissue region corresponding to the effect of the pharmacological agent. In one embodiment, the IPG 14 varies the energy level of the delivered electrical energy in inverse proportion to the effect of the pharmacological agent on the patient during a therapeutic window of the pharmacological agent. For this, the IPG 14 may be configured with a variety of stimulation inputs.

In a first example, the IPG 14 is configured with a pre-defined electrical modulation curve representative of the desired effect of the electrical energy delivered to a tissue in the patient during a therapeutic window of a pharmacological agent. In a second example, the IPG 14 is configured with a pre-defined pharmacological curve representative of the effect of a particular pharmacological agent on the patient. Such effect may be determined through various clinical tests performed on the patient over a particular period of time for that pharmacological agent. Subsequently, the IPG 14 may automatically vary the delivered electrical energy level in inverse proportion to this pre-defined pharmacological curve. In a third example, the sensor 37 may detect the absorption level of the pharmacological agent in the body of the patient and communicate the same to the IPG 14. Accordingly, the IPG 14 delivers the electrical energy in inverse proportion to the detected absorption level, which is indicative of the effect of pharmacological agent on the patient for a controlled electrical neuromodulation therapy.

Figure 4:
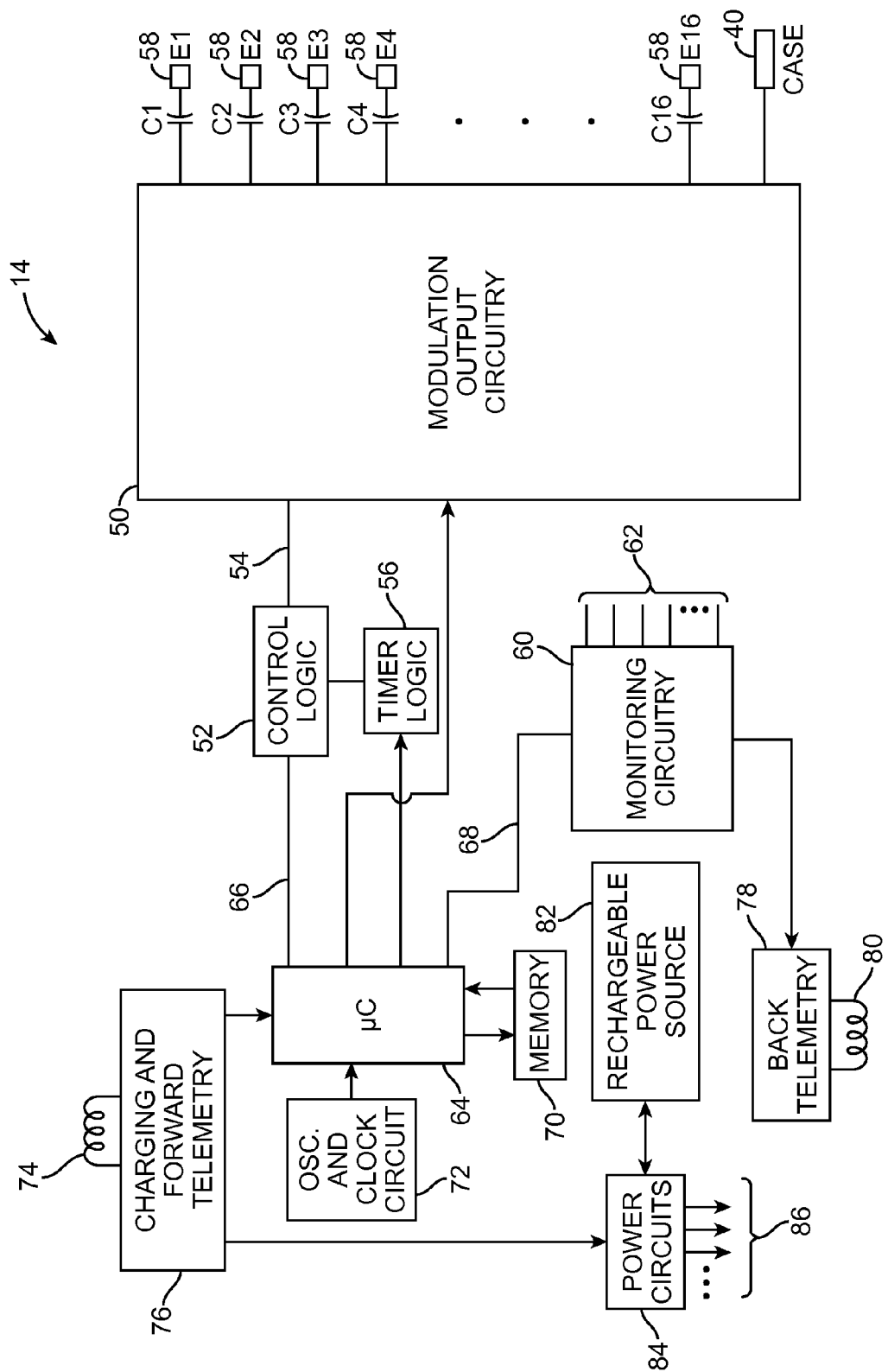
FIG. 4 is a block diagram of the internal components of the IPG of FIG. 3.

Turning next to FIG. 4, the internal components of the IPG 14 will now be described. The IPG 14 includes modulation output circuitry 50 configured for generating electrical modulation energy in accordance with an electrical pulse train having a specified pulse amplitude, pulse rate, pulse width, duty cycle, burst rate, and shape under control of control logic 52 over data bus 54. Control of the pulse rate and duration is facilitated by analog circuitry, or digital timer logic circuitry 56 controlling the analog circuitry, and which may have a suitable resolution, e.g., 10 µs. In alternative embodiments, a continuous modulating waveform may be generated by the modulation output circuitry 50 in a manner described in U.S. Provisional Patent Application Ser. No. 61/646,773, entitled "System and Method for Shaped Phased Current Delivery," which is expressly incorporated herein by reference. The modulation energy generated by the modulation output circuitry 50 is output via capacitors C1-C16 to electrical terminals 58 corresponding to electrodes E1-E16.

The modulation output circuitry 50 may either comprise independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this modulation output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. The monitoring circuitry 60 is also configured for receiving the detected absorption level of the pharmacological agent in the patient body from the sensor 37. The IPG 14 further comprises processing circuitry in the form of a microcontroller (µC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation parameters. In controlling the operation of the IPG 14, the microcontroller 64 is able to individually generate electrical energy at the electrodes 26 (see FIG. 3) using the modulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided. Significant to the present inventions, the microcontroller 64 manages the neuromodulation therapy in conjunction with pharmacological therapy, such that the patient receives an optimal level of therapy to treat the chronic pain. In particular, based on the present therapeutic effect of the pharmacological agent absorbed by the patient, the microcontroller 64 varies the level of the electrical energy delivered from the modulation output circuitry 50 to the target tissue of the patient by varying the pulse amplitude and/or pulse width, in conjunction with the pharmacological therapy provided by the absorption of the pharmacological agent within the patient. In one embodiment, the microcontroller 64 automatically instructs the modulation output circuitry 50 to vary the level of the electrical modulation energy delivered to the patient based on the sensed level of pharmacological agent acquired by the monitoring circuitry 60. Alternatively or optionally, the microcontroller 64 may automatically instruct the modulation output circuitry 50 to vary the level of the electrical modulation energy delivered to the patient based on pre-defined reference curves, such as electrical modulation curves and pharmacological curves, stored within the memory 70. Alternatively, the microcontroller 64 may so instruct the modulation output circuitry 50 in response to user input through the RC 16 or CP 18.

The IPG 14 further comprises an alternating current (AC) receiving coil 74 for receiving programming data (e.g., the operating program and/or modulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 5:
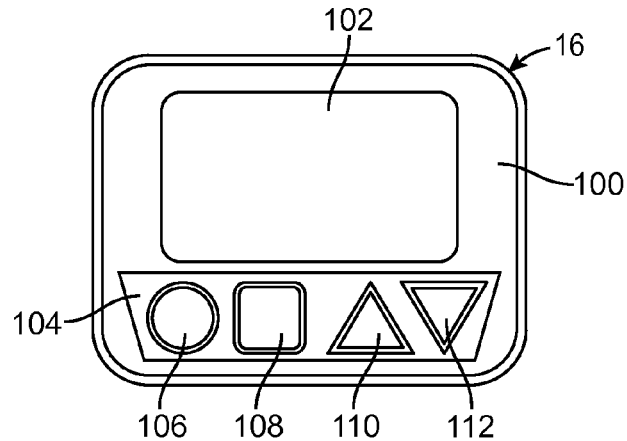
FIG. 5 is a plan view of a hand-held remote control (RC) that can be used in the SCM system of FIG. 1.

Referring now to FIG. 5, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can be actuated to increase or decrease any of modulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

Figure 6:
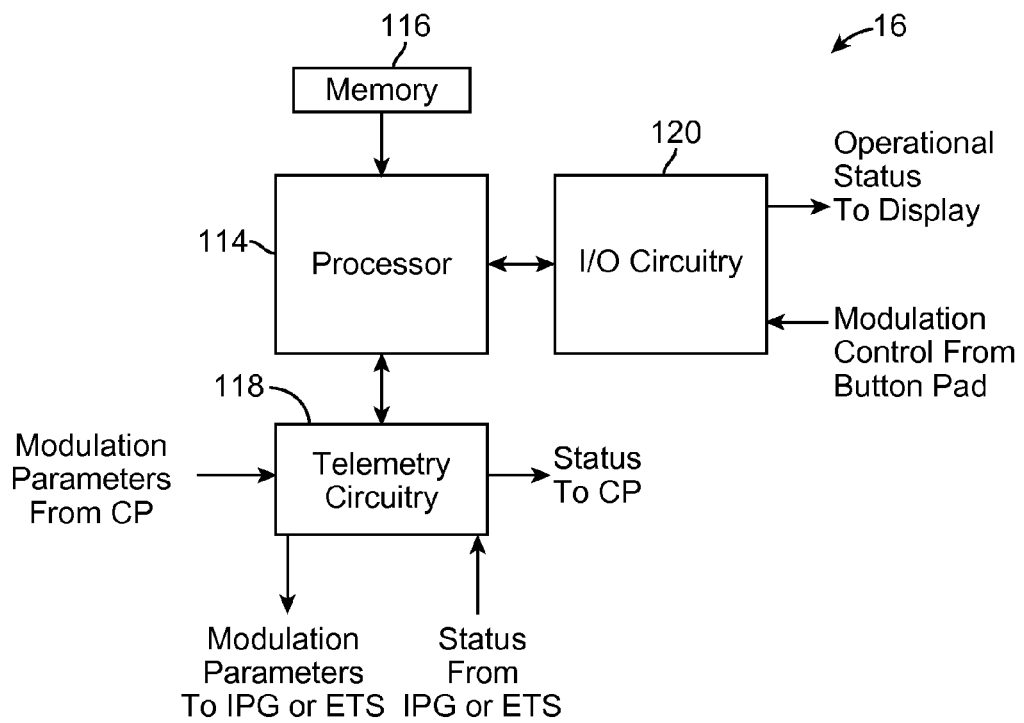
FIG. 6 is a block diagram of the internal components of the RC of FIG. 1.

Referring to FIG. 6, the internal components of an exemplary RC 16 will now be described. The RC 16 generally includes a processor 114 (e.g., a microcontroller), memory 116 that stores an operating program for execution by the processor 114, as well as modulation parameters, input/output circuitry, and in particular, telemetry circuitry 118 for outputting modulation parameters to the IPG 14 and receiving status information from the IPG 14, and input/output circuitry 120 for receiving modulation control signals from the button pad 104 and transmitting status information to the display screen 102 (shown in FIG. 5). As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the IPG 14 via the telemetry circuitry 118, thereby adjusting the modulation parameters stored in the IPG 14 and/or programming the IPG 14. The telemetry circuitry 118 can also be used to receive modulation parameters from the CP 18. Further details of the functionality and internal componentry of the RC 16 are disclosed in U.S. Pat. No. 6,895,280, which has previously been incorporated herein by reference.

Significant to the present inventions, the RC 16 may also be operated to instruct the IPG 14 to initiate the automated electrical energy adjustment technique. For example, the button pad 104 of the RC 16 may be operated by the user to prompt initiation of the automated electrical energy adjustment technique. Alternatively, the IPG 14 initiates the automated electrical energy adjustment technique without prompting by the RC 16; for example, once the IPG 14 senses the pharmacological agent. In the case where predefined reference curves are used in the automated electrical energy adjustment technique, the RC 16 is configured for receiving the previously described pre-defined reference curves from the CP 18 or any other programming system, and communicate the same to the IPG 14 for storage therein. Alternatively or additionally, the RC 16, when in the Pulse Amplitude Adjustment Mode or the Pulse Width Adjustment mode, is capable of adjusting the pulse amplitude and pulse width of the electrical energy generated by the IPG 14 and delivered to a tissue within a therapeutic window of the pharmacological agent.

Similarly, the CP 18 generally includes a processor (e.g., a central processor unit (CPU)) and memory that stores a stimulation programming package, which can be executed by the processor to allow a clinician to program the IPG 14 and RC 16. The memory also stores data defining various pulse amplitude-pulse width lines. In performing this function, the processor generates a plurality of stimulation parameter sets from the parameter values manually varied by the user via operation of the user input device or otherwise automatically varied by the processor itself. The CP 18 further includes output circuitry (e.g., via the telemetry circuitry of the RC 16) for downloading stimulation parameters to the IPG 14 and RC 16 and for uploading stimulation parameters already stored in the memory 116 of the RC 16, via the telemetry circuitry 118 of the RC 16 (see FIG. 6). To allow the clinician to perform these functions, the CP 18 includes a user input device (e.g., a mouse and keyboard), and a display monitor housed in a case.

Further details discussing user interfaces and exemplary stimulation programming packages are described in U.S. Pat. No. 6,393,325 and U.S. Patent Application Ser. No. 61/080,187, entitled "System and Method for Converting Tissue Stimulation Programs in a Format Usable by an Electrical Current Steering Navigator," which are expressly incorporated herein by reference.

Although the electrical energy adjustment technique has been described as being implemented within the IPG 14, it should be appreciated that this technique can be implemented in the RC 16 or CP 18, in which case, the detected absorption level of the pharmacological agent will be continually transmitted from the IPG 14 to the RC 16 and/or CP 18 for use by the electrical energy adjustment technique. In the case where pre-defined reference curves are used by the electrical energy adjustment technique, these reference curves can be stored in the RC 16 and/or CP 18. In either case, the RC 16 and/or CP 18 will instruct the IPG 14 to vary the electrical energy in response to the detected absorption level or in accordance with the pre-defined reference curves.

Figure 7:
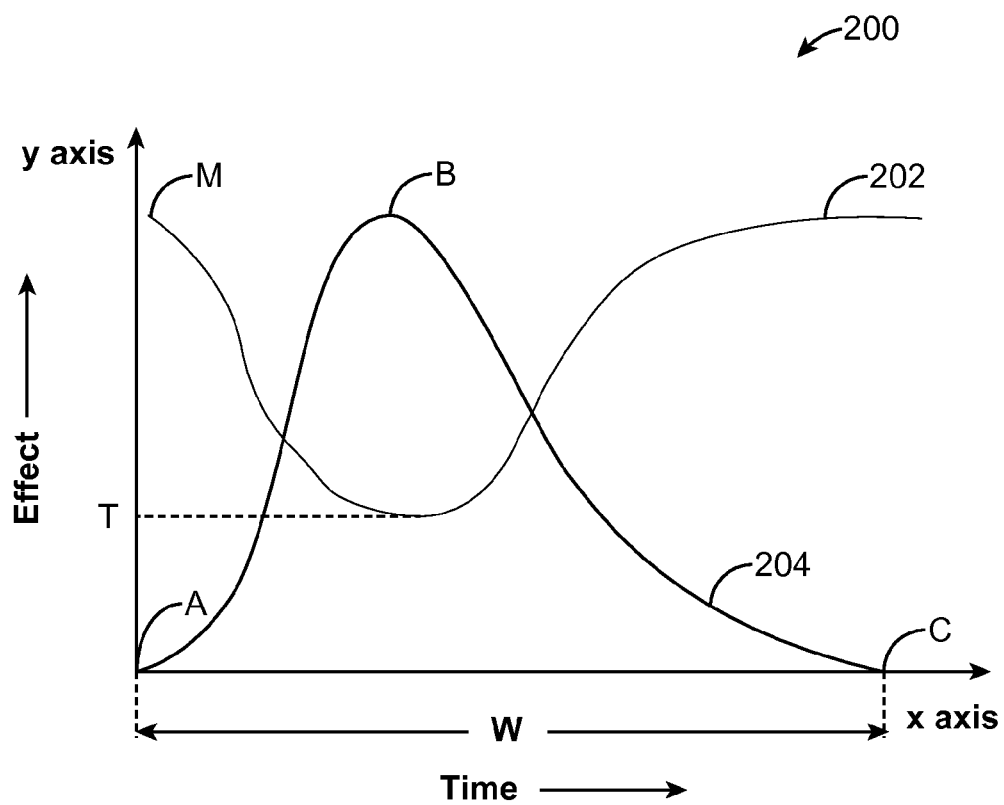
FIG. 7 illustrates an exemplary response of neuromodulation therapy relative to the effect of pharmacological agent in a body during the its therapeutic window.

Having described the structure and function of the SCM system 10, a method for performing neuromodulation therapy in conjunction with pharmacological therapy in a patient will be described. Referring first to FIG. 7, a graph 200 illustrates an exemplary response of neuromodulation therapy (represented by the curve 202) relative to the effect of pharmacological therapy (represented by the curve 204) during the therapeutic window 'W' of the pharmacological therapy. The time taken by the pharmacological agent for providing the intended effect through its therapeutic range is defined as its therapeutic window 'W'. Typically, the effect of pharmacological agent is cyclic and non-linear in nature, such that the effect is relatively stronger after an initial reaction time and then tends to weaken as time lapses.

For example, within a standard 4-hour therapeutic window, the effect of pharmacological agent may be relatively stronger in a first time period, i.e., the first hour, when the absorption level of the pharmacological agent is relatively high and relatively weaker when the absorption level of the pharmacological agent is relatively low in a second time period, i.e., the last hour. The second time period is subsequent to the first time period of the therapeutic window of the pharmacological agent. Accordingly, as illustrated, a pharmacological agent consumed by a patient at point A may have an approximately zero therapeutic effect in the body. The pharmacological agent may be defined as any substance or molecule capable of providing therapy for treatment of a medical condition.

The consumed pharmacological agent is absorbed and distributed within the body through body fluids such as blood, spinal fluid, bile, and so on, and provides pharmacological therapy to a patient. The absorption level of the pharmacological agent may increase over time to point B at which the pharmacological agent has the maximum intended effect. Subsequently, the effect of pharmacological agent may begin to gradually weaken such that the desired effect of pharmacological agent reduces over time to point C along the curve 204. At point C, the effect of pharmacological agent is again approximately zero.

The curve 204 along the points A, B, and C is non-linear and defines a therapeutic range of the pharmacological agent within which different concentrations of the pharmacological agent yield the intended effect without toxicity. This difference in concentrations of the pharmacological agent may be due to varying absorption levels of the pharmacological agent in the body. The toxicity of the pharmacological agent may be defined by the presence of unwanted or harmful concentration of the pharmacological agent in the body. In order to compensate for the non-linear effect of pharmacological agent, the energy level of the electrical energy applied to a tissue for neuromodulation therapy may be adjusted accordingly.

As illustrated, the applied neuromodulation therapy, shown by the curve 202, may be modulated in inverse proportion to the effect of pharmacological agent under predefined threshold levels within the therapeutic window 'W' of the pharmacological agent. As such, when the effect of the pharmacological agent is approximately zero at point A, the energy level of the applied electrical energy should be set to a maximum value M, which produces a therapeutic effect that is at least not less than the peak effect of pharmacological agent at point B. As the effect of pharmacological agent rises along the curve 204 from point A to point B, the controller/processor of IPG 14 may be configured to instruct the modulation output circuitry to reduce the intensity of stimulation parameters, such as pulse width and/or pulse amplitude of electrical current. Accordingly, the energy level of the applied electrical energy neuromodulation may gradually decrease the neuromodulation therapy to a pre-defined threshold value T based on the change in the effect of pharmacological agent due to its varying parameters, such as absorption level, during the pharmacological agent therapeutic window 'W'.

Subsequently, when the effect of pharmacological agent begins to decrease from point B to point C on the curve 204, the neuromodulation therapy may be again increased to at least the maximum value M along the curve 202. In order to achieve such a tandem and uniform operation between the neuromodulation and pharmacological therapies, a user may operate the clinician's programmer 18 to telemetrically program the microcontroller 64 of IPG 14 based on an information set. This information set may include the curve 204 and the information related to the therapeutic window of the pharmacological agent, both of which may be pre-determined through various clinical tests performed on a patient for a particular duration. The information set may further include the electrical modulation curve 202, which is pre-defined in inverse proportion to the effect of the pharmacological agent on the patient during the therapeutic window W, represented by the curve 204. The information set may then be stored in the memory 70 of the IPG 14. Also, such tandem operation reduces the loss of electrical energy, as well as avoids an overlap between the intended effects of the neuromodulation and pharmacological therapies, while the pharmacological agent is in effect.

Figure 8A:
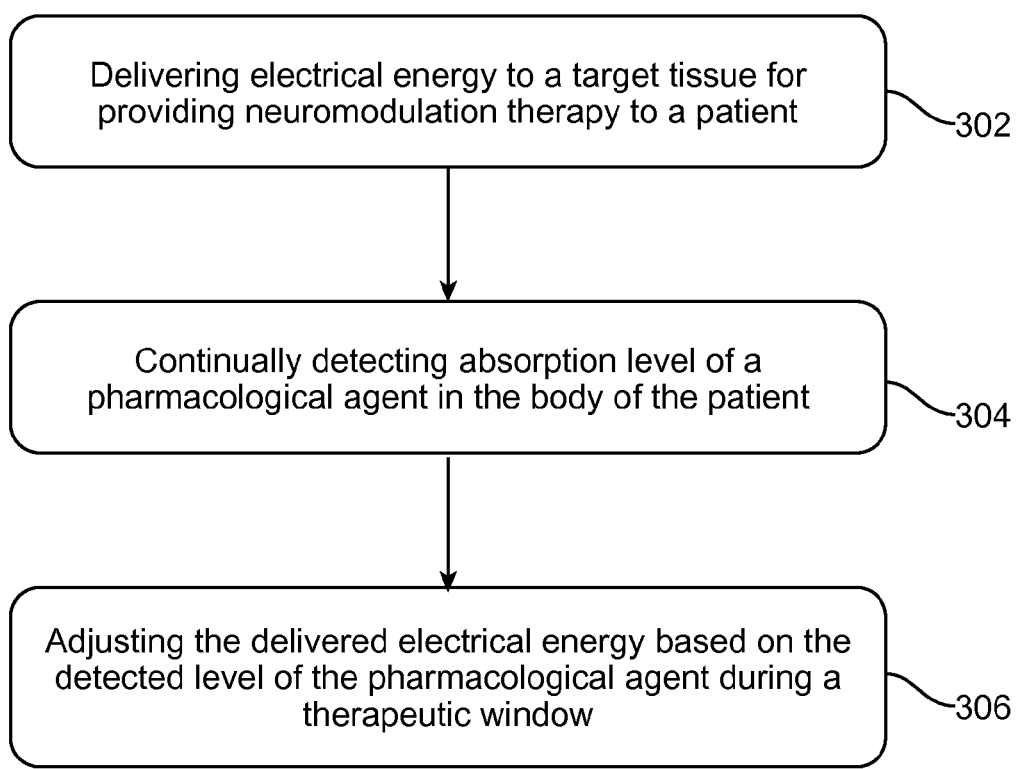
FIGS. 8A and 8B illustrate exemplary methods for configuring IPG in FIG. 3 according to an embodiment of the present disclosure.

Referring now to FIG. 8A, a first exemplary method for operating the SCM system 10 to perform neuromodulation therapy in conjunction with the provision of pharmacological therapy to a patient will be described. Such a patient may be suffering from a medical condition, such as chronic pain. This method can be implemented in the general context of computer executable instructions. Generally, computer executable instructions may include but are not limited to routines, programs, objects, components, data structures, procedures, modules, functions, and the like that perform particular functions or implement particular abstract data types. The computer executable instructions may be stored on a computer readable medium and may be loaded or embedded in an appropriate device for execution.

At step 302, the SCM system 10 is operated to deliver electrical energy to target tissue region of the patient, thereby modulating (e.g., stimulating) the target tissue region. In the illustrated embodiment, the microcontroller 64 of the IPG 14 instructs the modulation output circuitry 50 to deliver the electrical energy to the target tissue region via the neuromodulation leads 12.

At step 304, the SCM system 10 continually (e.g., continuously or periodically) detects the absorption level of a pharmacological agent in the patient. In the illustrated embodiment, the pharmacological agent is sensed by the sensor 37 and communicated to the monitoring circuitry 60 of the IPG 14. The patient may be given a particular pharmacological agent for treatment of the medical condition along with the neuromodulation therapy. Once consumed, the pharmacological agent is broken down by metabolites to make the pharmacological agent suitable for absorption and distribution inside the body of the patient. The broken down pharmacological agent may be absorbed by body fluids such that the level of pharmacological agent absorbed in the body may vary during its therapeutic window as discussed in FIG. 7.

At step 306, the SCM system 10 automatically adjusts the level of the delivered electrical energy based on the detected absorption level of the pharmacological agent during a therapeutic window of the pharmacological agent; for example, by adjusting the pulse amplitude and/or pulse width. In the illustrated embodiment, the microcontroller 64 of the IPG 14 instructs the modulation output circuitry 50 to adjust the level of the delivered electrical energy delivered. This automatic adjustment of electrical energy may be in inverse proportion to the detected absorption level, which defines the effect of the pharmacological agent during its therapeutic window.

Figure 8B:
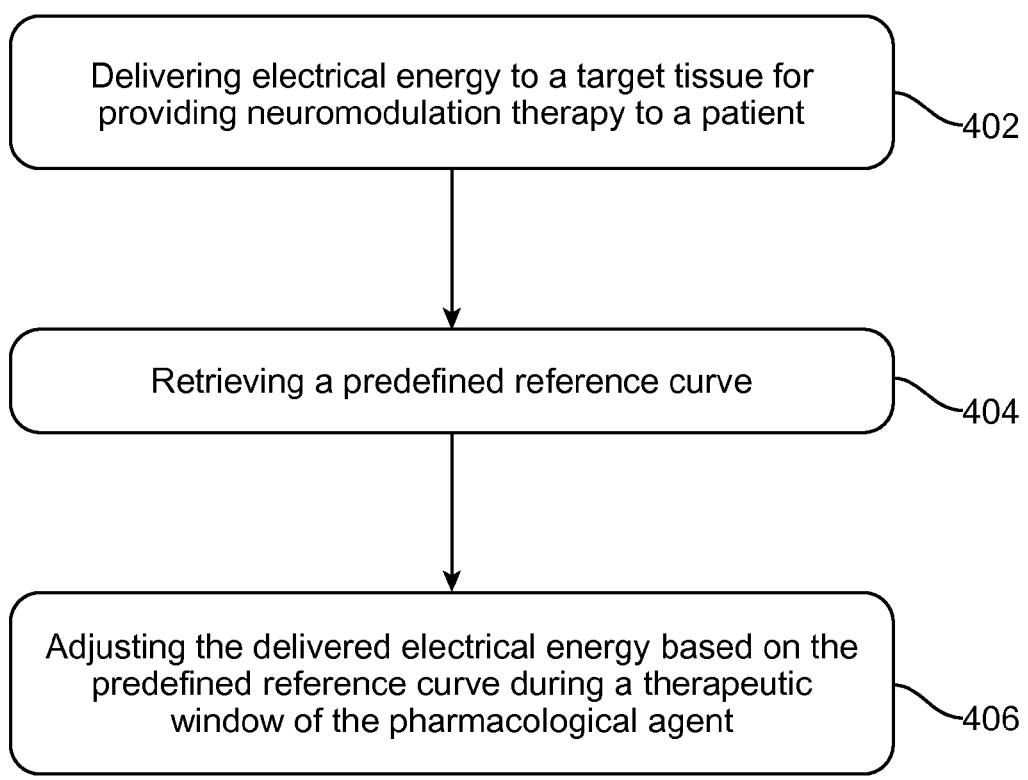

Referring to FIG. 8B, a second exemplary method for operating the SCM system 10 to perform neuromodulation therapy in conjunction with the provision of pharmacological therapy to a patient will be described. In contrast to FIG. 8A, the method of operation in FIG. 8B utilizes a pre-defined reference curve, instead of a detected absorption level of the pharmacological agent, to vary the level of the electrical energy delivered to the target tissue region.

At step 402, the SCM system 10 is operated to deliver electrical energy to target tissue region of the patient, thereby modulating (e.g., stimulating) the target tissue region. In the illustrated embodiment, the microcontroller 64 of the IPG 14 instructs the modulation output circuitry 50 to deliver the electrical energy to the target tissue region via the neuromodulation leads 12.

At step 404, the SCM system 10 retrieves a pre-defined reference curve In the illustrated embodiment, the microcontroller 64 retrieves a pre-defined reference curve from the memory 70 of the IPG 14. In a first example, the pre-defined reference curve is an electrical modulation curve (e.g., similar to the electrical modulation curve 202 in FIG. 7) that defines the stimulation trajectory at which the electrical energy is automatically delivered to a tissue in the patient, within the therapeutic window of the pharmacological agent. In another example, the pre-defined reference curve is a pharmacological curve (e.g., similar to the pharmacological curve 204 in FIG. 7) that defines the effect of the pharmacological agent in the patient body within the therapeutic window of the pharmacological agent. This pre-defined pharmacological curve may be determined through various clinical tests conducted on the patient over a pre-determined time.

At step 406, the SCM system 10 automatically adjusts the level of the delivered electrical energy in accordance with the retrieved pre-defined reference curve; for example, by adjusting the pulse amplitude and/or pulse width. In the illustrated embodiment, the microcontroller 64 of the IPG 14 instructs the modulation output circuitry 50 to adjust the level of the delivered electrical energy delivered. In the case where the recalled pre-defined reference curve is an electrical modulation curve, the microcontroller 64 dynamically varies the delivered electrical energy to the tissue according to the recalled electrical modulation curve during a therapeutic window of the pharmacological agent. In the case where the recalled pre-defined reference curve is a pharmacological curve the microcontroller 64 dynamically varies the delivered electrical energy to the tissue in inverse proportion to the recalled pharmacological curve during a therapeutic window of the pharmacological agent. In both cases, the electrical energy adjustment may be triggered by user input to the RC 16 and/or CP 18 or may be periodically triggered in accordance with a programmed schedule.

In alternative embodiments, information associated with the pharmacological regimen provided to the patient may be entered into the RC 16 and/or CP 18. Such information may include, but not be limited to, the time that the pharmacological agent was administered to the patient, the time elapsed since the intake of the pharmacological agent, the amount of the pharmacological agent administered, therapeutic range, half life, and plasma concentration of the pharmacological agent in the body during its therapeutic window.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system for managing electrical neuromodulation therapy for a patient in conjunction with administering a pharmacological agent to the patient, the neuromodulation system comprising:
   output modulation circuitry configured for delivering electrical energy to a target tissue region of the patient, thereby electrically modulating the target tissue region and providing therapy to the patient;
   a sensor configured for detecting an absorption level of the pharmacological agent in a body of the patient;
   monitoring circuitry operably connected to the sensor and configured for continually monitoring the absorption level of the pharmacological agent in the patient; and
   a controller/processor configured for automatically instructing the output modulation circuitry to vary an energy level of the electrical energy delivered to the tissue during a therapeutic window based on the monitored absorption level of the pharmacological agent.

2. The neuromodulation system of claim 1, wherein the monitored absorption level of the pharmacological agent is relatively high during a first time period of the therapeutic window and relatively low during a second time period subsequent to the first time period, and the controller/processor is configured for automatically instructing the output modulation circuitry to deliver the electrical energy to the tissue at a relatively low level during the first time period and at a relatively high level during the second time period.

3. The neuromodulation system of claim 1, wherein the electrical energy comprises pulsed electrical energy, and the controller/processor is configured for automatically instructing the output modulation circuitry to automatically vary the level of the electrical energy by adjusting a pulse width of the pulsed electrical energy.

4. The neuromodulation system of claim 1, further comprising a user interface configured for receiving a user input, wherein the controller/processor is configured for triggering the automatic instruction of the output modulation circuitry to vary the energy level of the electrical energy delivered to the tissue in response to the user input.

5. The neuromodulation system of claim 1, wherein the output modulation circuitry is configured to generate a continuous modulating waveform.

6. The neuromodulation system of claim 1, wherein the output modulation circuitry is configured to generate a pulse train under control of control logic to provide a specified shape.

7. The neuromodulation system of claim 1, wherein the output modulation circuitry is configured to deliver the electrical energy in inverse proportion to the detected absorption level.

8. The neuromodulation system of claim 1, wherein the output modulation circuitry is configured for delivering pulse trains, and the controller/processor is configured for automatically instructing the output modulation circuitry to automatically vary the pulse train based on the monitored absorption level of the pharmacological agent.

9. The neuromodulation system of claim 1, wherein the electrical energy comprises pulsed electrical energy, and the controller/processor is configured for automatically instructing the output modulation circuitry to automatically vary the level of the electrical energy by adjusting a pulse amplitude of the pulsed electrical energy.

10. The neuromodulation system of claim 1, further comprising memory storing a pre-defined electrical modulation curve, wherein the controller/processor is configured for automatically instructing the output modulation circuitry to vary the energy level of the electrical energy delivered to the tissue in accordance with the pre-defined electrical modulation curve.

11. A method for managing electrical neuromodulation therapy for a patient in conjunction with administering a pharmacological agent to the patient, the method comprising:
   delivering electrical energy to a target tissue region of the patient, thereby electrically modulating the target tissue region providing therapy to the patient;
   continually detecting an absorption level of the pharmacological agent in the patient wherein continually detecting the absorption level includes using a sensor configured for detecting the absorption level in a body of the patient; and
   automatically varying an energy level of the electrical energy delivered to the tissue based on the detected absorption level of the pharmacological agent during a therapeutic window.

12. The method of claim 11, wherein continually detecting the absorption level of the pharmacological agent in the patient comprises detecting a relatively high absorption level of the pharmacological agent during a first time period of the therapeutic window and detecting a relatively low absorption level during a second time period subsequent to the first time period, and the energy level of the electrical energy delivered to the tissue is relatively low during the first time period and relatively high during the second time period.

13. The method of claim 11, wherein the electrical energy delivered to the tissue comprises pulsed electrical energy, the energy level of which is automatically varied by adjusting a pulse width of the pulsed electrical energy.

14. The method of claim 11, wherein the automatic varying of the energy level of the electrical energy delivered to the tissue is immediately triggered in response to a user input.

15. The method of claim 11, wherein automatically varying the energy level of the electrical energy includes delivering the electrical energy in inverse proportion to the detected absorption level.

16. The method of claim 11, wherein delivering electrical energy includes delivering a continuous modulating waveform.

17. The method of claim 11, wherein delivering electrical energy includes delivering a pulse train under control of control logic to provide a specified shape.

18. The method of claim 11, wherein delivering electrical energy includes delivering pulse trains, and automatically varying the energy level includes automatically vary the pulse train based on the detected absorption level of the pharmacological agent.

19. The method of claim 11, wherein the electrical energy delivered to the tissue comprises pulsed electrical energy that is automatically varied by adjusting a pulse amplitude of the pulsed electrical energy.

20. The method of claim 11, wherein the energy level of the electrical energy delivered to the tissue is automatically varied in accordance with a pre-defined electrical modulation curve.

* * * * *